United States Patent
Margalit et al.

(10) Patent No.: US 8,501,237 B2
(45) Date of Patent: Aug. 6, 2013

(54) FORMULATIONS OF WATER INSOLUBLE OR POORLY WATER SOLUBLE DRUGS IN LIPIDATED GLYCOSAMINOGLYCAN PARTICLES AND THEIR USE FOR DIAGNOSTICS AND THERAPY

(75) Inventors: Rimona Margalit, Givatayim (IL); Noga Yerushalmi, Nes-ziona (IL); Dan Peer, Kiryat Uno (IL); Ilia Rivkin, Rehovot (IL)

(73) Assignee: Tel-Aviv University Future Technology Development L.P., Tel-Aviv (IL)

( * ) Notice: Subject to any disclaimer, the term of this patent is extended or adjusted under 35 U.S.C. 154(b) by 0 days.

(21) Appl. No.: 13/420,069

(22) Filed: Mar. 14, 2012

(65) Prior Publication Data
US 2012/0171261 A1   Jul. 5, 2012

Related U.S. Application Data

(63) Continuation of application No. 11/718,485, filed as application No. PCT/US2005/039224 on Nov. 2, 2005, now Pat. No. 8,178,129.

(60) Provisional application No. 60/623,862, filed on Nov. 2, 2004.

(51) Int. Cl.
A61K 9/14 (2006.01)
(52) U.S. Cl.
USPC .................... 424/489; 424/450; 424/499
(58) Field of Classification Search
USPC ................................. 424/489, 450
See application file for complete search history.

(56) References Cited

U.S. PATENT DOCUMENTS

| | | | |
|---|---|---|---|
| 5,401,511 | A | 3/1995 | Margalit |
| 5,733,892 | A | 3/1998 | Sakurai et al. |
| 6,458,382 | B1 | 10/2002 | Herweijer et al. |
| 7,544,374 | B2 | 6/2009 | Margalit et al. |
| 2002/0131995 | A1 | 9/2002 | Szoka, Jr. |
| 2004/0127459 | A1* | 7/2004 | Dehayza et al. ........... 514/54 |
| 2005/0203054 | A1* | 9/2005 | Yedgar ...................... 514/54 |

FOREIGN PATENT DOCUMENTS

| | | |
|---|---|---|
| WO | 90/07469 A1 | 7/1990 |
| WO | 00/01366 A1 | 1/2000 |
| WO | 00/41687 A2 | 7/2000 |
| WO | 02/00194 A2 | 1/2002 |
| WO | 02/45689 A1 | 6/2002 |
| WO | 03015755 A1 | 2/2003 |
| WO | 2004/009075 A1 | 1/2004 |

OTHER PUBLICATIONS

The Dorland's Illustrated Medical Dictionary, 30th edition, Saunders, Philadelphia, PA, 2003, p. 1058.
The Merriam-Webster Dictionary online definition of "liposome" (webpage from 2008).
The Encyclopedia Britannica online definition of "liposome" (webpage from 2008).
Torchilin, V.P., Nature Rev. Drug Disc., 5:145-160 (2005).
Rivkin et al., "Paclitaxel-clusters coated with hyaluronan as selective tumor-targeted nanovectors", Biomaterials 31:7106-7114 (2010).

\* cited by examiner

*Primary Examiner* — Gollamudi Kishore
(74) *Attorney, Agent, or Firm* — Browdy and Neimark, PLLC

(57) ABSTRACT

The invention provides a formulation of water insoluble or poorly water soluble drugs encapsulated in lipidated glycosaminoglycan particles for targeted drug delivery.

24 Claims, 10 Drawing Sheets

Production process for insoluble drugs

1. Lipid & drug dissolution
Organic solvent: ethanol
Lipid choices: DPPE or DLPE
Incubation period: ~15 minutes
Incubation temperature: 44°C/DLPE, 65°C/DPPE
Rotary evaporation

2. HA activation
Dissolution: in water
Buffering: Acetate 0.1 M, pH=4.5
Activation: EDC addition
Incubation: 120 minutes at 37°C

▼

3. Generating a lipid-drug suspension
Buffer: Borate 0.1M, pH=9.0
Incubation period: ~15 minutes
Incubation temperature: 44°C/DLPE, 65°C/DPPE

4. Adjusting pH to 9.0
Incubation: overnight,

▼

5. Separations, washings, reduction to physiological pH

▼

6. Lyophilization:

Figure 7

FORMULATIONS OF WATER INSOLUBLE OR POORLY WATER SOLUBLE DRUGS IN LIPIDATED GLYCOSAMINOGLYCAN PARTICLES AND THEIR USE FOR DIAGNOSTICS AND THERAPY

CROSS-REFERENCE TO RELATED APPLICATIONS

The present application is a continuation of application Ser. No. 11/718,485, filed Apr. 21, 2008, which is a 371 national stage of international application no. PCT/US2005/039224, filed Nov. 2, 2005, which claims the benefit of priority under 35 U.S.C. §119(e) from provisional U.S. application No. 60/623,862, filed Nov. 2, 2004, the entire content of which is herein incorporated by reference.

BACKGROUND OF THE INVENTION

1. Field of the Invention

The present invention relates to drug delivery and formulation and specifically to particles of lipidated glycosaminoglycans encapsulating water insoluble or poorly water soluble drugs and their use in diagnosing and treating pathological conditions.

2. Description of the Related Art

Glycosaminoglycans, or mucopolysaccharides, along with collagen, are the chief structural elements of all connective tissues. Glycosaminoglycans, or gags, are large complexes of polysaccharide chains associated with a small amount of protein. These compounds have the ability to bind large amounts of water, thereby producing a gel-like matrix that forms the body's connective tissues. Gags are long chains composed of repeating disaccharide units (aminosugar-acidic sugar repeating units). The aminosugar is typically glucosamine or galactosamine. The aminosugar can also be sulfated. The acidic sugar may be D-glucuronic acid or L-iduronic acid. In vivo, gags other than hyaluronic acid are covalently bound to a protein, forming proteoglycan monomers. The polysaccharide chains are elongated by the sequential addition of acidic sugars and aminosugars.

Among the most common gags are hyaluronic acid, keratan sulfate, chondroitin sulfate, heparin sulfate, and dermatin sulfate. Gags may be chemically modified to contain more sulfur groups than in their initially extracted form. In addition, gags may be partially or completely synthesized and may be of either plant or animal origin.

Hyaluronic acid is a naturally occurring member of the glycosaminoglycan family which is present in particularly high concentration in the cartilage and synovial fluid of articular joints, as well as in vitreous humor, in blood vessel walls, and umbilical cord and other connective tissues. Hyaluronic acid can be in a free form, such as in synovial fluid, and in an attached form, such as an extracellular matrix component. This polysaccharide consists of alternating N-acetyl-D-glucosamine and D-glucuronic acid residues joined by alternating β-1,3-glucuronidic and β-1,4-glucosaminidic bonds. In water, hyaluronic acid dissolves to form a highly viscous fluid. The molecular weight of hyaluronic acid isolated from natural sources generally falls within the range of $5 \times 10^4$ up to $10^7$ daltons. Hyaluronic acid has a high affinity for the extracellular matrix and to a variety of tumors, including those of the breast, brain, lung, skin, and other organs and tissues.

Drug delivery systems are used for maintaining a constant blood level of a drug over a long period of time by administering a drug into the body, or for maintaining an optimal concentration of a drug in a specific target organ by systemic or local administration, and over a prolonged period of time. For instance, chemically modified hyaluronic acid can be used for controlled release drug delivery. Balazs et al, in U.S. Pat. No. 4,582,865, reported that cross-linked gels of hyaluronic acid can slow down the release of a low molecular weight substance dispersed therein but not covalently attached to the gel macromolecular matrix. Other forms of pharmaceutical preparations/formulations are used as drug delivery systems, including the use of a thin membrane of a polymer or the use of a liposome as a carrier for a drug.

There are two basic classes of drug carriers: particulate systems, such as cells, microspheres, viral envelopes, and liposomes; and non-particulate systems, which are usually soluble systems, consisting of macromolecules such as proteins or synthetic polymers.

The majority of drug dosage forms available in the clinic (over 99%) are however formulations of free drugs. Nevertheless, microscopic and submicroscopic particulate carriers, performing as drug delivery systems, are used to improve clinical outcomes compared to treatment with free drug. Enclosure within a carrier protects the drug from the biological environment, reducing the risk of degradation and inactivation. Encapsulation also protects the biological environment from indiscriminate distribution of free drug, reducing the risk of toxicity and adverse side effects. Carrier mediation reduces pre-mature drug clearance and ensures a constant blood level of drug and/or an optimal concentration of drug in target organs over a prolonged period of time by systemic or by local administration. Particulate carriers perform as sustained-release or controlled-release drug depots, thereby contributing to improved drug efficacy and allowing reduction in dosing frequency.

Despite the advantages offered, there are some difficulties associated with using drug encapsulating biopolymers. For example, biopolymers structured as microparticulates or nanoparticulates have limited targeting abilities, limited retention and stability in circulation, potential toxicity upon chronic administration, and the inability to extravasate. Numerous attempts have been made to bind different recognizing substances, including antibodies, glycoproteins, and lectins, to particulate systems, such as liposomes, microspheres, and others, in order to confer upon them some measure of targeting. Although bonding of these recognizing agents to the particulate system has met with success, the resulting modified particulate systems did not perform as hoped, particularly in vivo.

Other difficulties have also arisen when using such recognizing substances. For example, antibodies can be patient-specific, and thereby add cost to the drug therapy. Additionally, not all binding between recognizing substrate and carrier is covalent. Covalent bonding is essential, as non-covalent binding might result in dissociation of the recognizing substances from the particulate system at the site of administration, due to competition between the particulate system and the recognition counterparts to the target site for the recognizing substance. Upon such dissociation, the administered modified particulate system can revert to a regular particulate system, thereby defeating the purpose of administration of the modified particulate system.

When it comes to drugs that have poor aqueous solubility (to be referred henceforth as poorly water-soluble and water insoluble drugs), there is further deficiencies in treatment with the free drug. In order to generate a dosage form that will allow treatment at all, it is necessary to formulate the water insoluble or poorly water soluble drug in a vehicle that will be hydrophobic enough to solubilize the drug, yet be hydrophilic enough to accommodate administration into an aqueous medium. These vehicles are usually detergent-like, such as the 1:1 blend of Cremophor EL (polyethoxylated caster oil) and ethanol used for paclitaxel. The drawback is that these vehicles and other similar detergent-based vehicles are highly toxic and cause hypersensitivity reaction and release of histamines in patients.

U.S. Pat. No. 5,733,892 to Sakurai et al. discloses lipidated glycosaminoglycan molecules which are soluble in aqueous solution. WO 03/015755 discloses a similar system of lipidated glycosaminoglycan particles which form suspensions of particles in an aqueous phase. The present invention is an improvement of the lipidated glycosaminoglycan particles of WO 03/015755 as none of the currently available delivery technologies provide a satisfactory solution to the problems associated with targeted delivery of water insoluble and poorly water soluble drugs.

Citation of any document herein is not intended as an admission that such document is pertinent prior art, or considered material to the patentability of any claim of the present application. Any statement as to content or a date of any document is based on the information available to applicant at the time of filing and does not constitute an admission as to the correctness of such a statement.

SUMMARY OF THE INVENTION

It is an object of the present invention is to overcome the deficiencies in the prior art.

Another object of the present invention to form lipidated glycosaminoglycan particles for encapsulating water insoluble or poorly water soluble drugs.

A further object of the present invention is to deliver such water insoluble or poorly water soluble drugs encapsulated in a lipidated glycosaminoglycan particle.

The present invention provides a formulation of water insoluble or poorly water soluble drugs encapsulated in lipidated glycosaminoglycan particles, also termed "gagomers". Such gagomers are bioadhesive biopolymers produced by cross-linking a lipid having a primary amino group to a carboxylic acid-containing glycosaminoglycan. Microparticles or nanoparticles are formed in a controlled manner with dominant particle diameter ranges of about 2-5 microns for microparticles and about 50-200 nanometers for nanoparticles. Small or large active ingredients/drugs which are water insoluble or poorly water soluble can be encapsulated/entrapped in these gagomer particles with high efficiency greater than 50%, and usually greater than 80%.

The present invention also provides a pharmaceutical composition containing a water insoluble or poorly water soluble drug/active ingredient encapsulated in lipidated glycosaminoglycan particles.

Other aspects of the present invention include a method for preparing the lipidated glycosaminoglycan particle encapsulated drug/active ingredient and a method for treating a subject suffering from a pathological condition by administering an effective amount of the water insoluble or poorly water soluble active ingredient/drug encapsulated in lipidated glycosaminoglycan particles.

A still further aspect of the present invention is directed to an improved method for treating an indication with a water insoluble or poorly water soluble drug that is effective for treating the indication, where the improvement is that the water insoluble or poorly water-soluble drug is administered encapsulated in lipidated glycosaminoglycan particles.

BRIEF DESCRIPTION OF THE DRAWINGS

FIG. 7 shows a scheme of the production process for the insoluble drugs loaded inside gagomers.

DETAILED DESCRIPTION OF THE INVENTION

Figure 1:
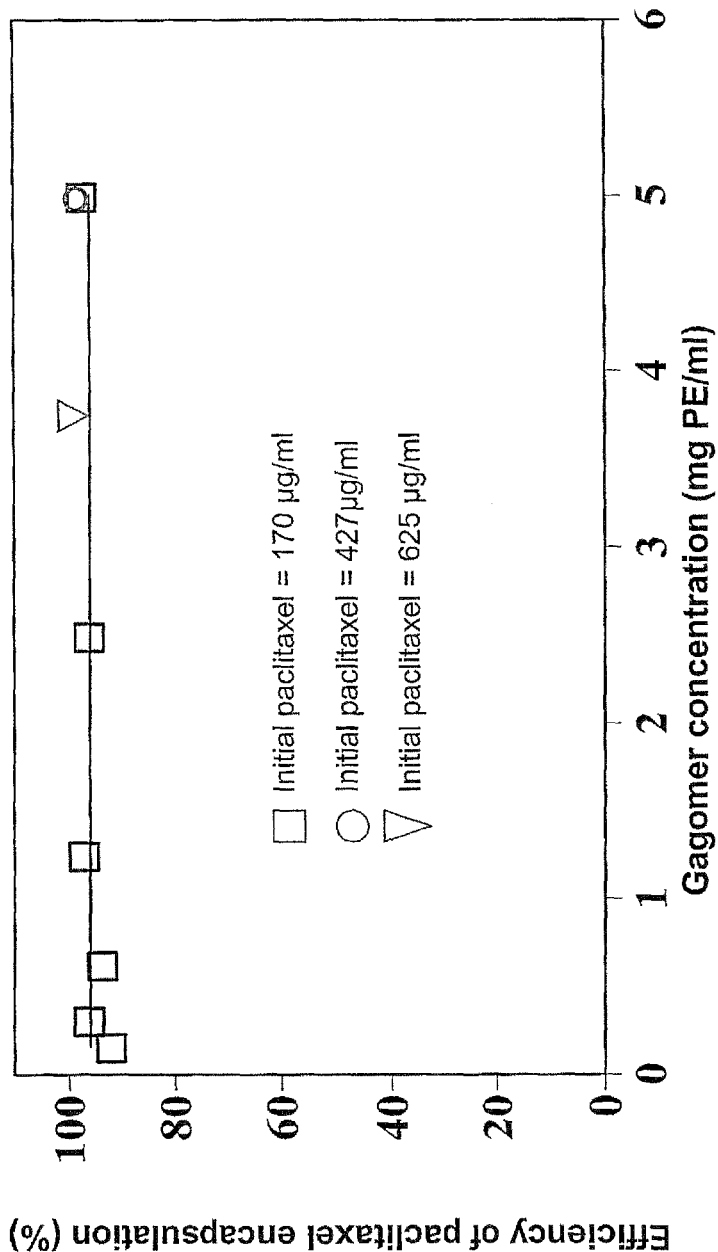
FIG. 1 is a graph showing the efficiency of paclitaxel encapsulation in gagomers, in the via-DMSO method, as a function of gagomer concentration (in units of mg PE/ml). The points are the experimental data obtained at different initial drug concentration as listed. The solid line and the error bars are the average encapsulation efficiency and sd for all data points.

Lipidated glycosaminoglycan particles, also termed "gagomers", are a novel drug delivery technology for water insoluble and poorly water soluble drugs/active ingredients that overcomes limitations and deficiencies of the prior art. This technology provides a versatile, multi-product drug delivery system with marked performance improvements in terms of both manufacturing processes and clinical outcomes. These gagomers have the ability to perform as site-adherent, site-retained, sustained release drug depots for systemic, topical, and regional administration. The introduction of this technology for use with water insoluble or poorly water soluble drugs is expected to significantly advance the state-of-the-art in targeted drug delivery modalities.

Gagomer particles are bioadhesive biopolymers prepared by reacting a glycosaminoglycan with at least one lipid, preferably a phospholipid such as phosphatidylethanolamine (PE), more preferably dilauryl phosphatidylethanolamine (DLPE) or dipalmitoyl phosphatidylethanolamine (DPPE) which differ in chain length, to crosslink the carboxylic acid groups in the glycosaminoglycan with a primary amine in the lipid. Preferably, a coupling agent of the carbodiimide type that forms a covalent bond between carboxyl residues of the glycosaminoglycan and the primary amine of the lipid is used for the crosslinking.

A unique feature of the gagomer technology discovered by the present inventors is that these carrier particles, by virtue of their internal lipid regions, provide an environment for solublization and encapsulation of water insoluble and poorly water soluble drugs without the need to include any of the toxic and adverse side effect-causing detergent-like vehicles. Gagomer particles therefore have the advantageous ability to perform as a targeted delivery system for water insoluble and poorly water soluble drugs. The water insoluble and poorly water soluble drugs are encapsulated in gagomer particles with high efficiency to form the drug encapsulating gagomer particles according to the present invention. The resultant formulations thus perform as sustained release drug depots which are stable in serum and retain drug activity at levels similar to or better than equivalent doses of free drug.

The present invention is directed to formulations of water insoluble or poorly water soluble drugs in gagomer particles, to pharmaceutical compositions containing the drug encapsulating gagomers, and to methods of preparation and use thereof.

A preferred embodiment of a poorly water soluble drug encapsulated in the gagomer particles according to the present invention is paclitaxel (taxol; TX), a cytotoxic drug that was first isolated from the bark of the pacific yew plant. Pacitaxel promotes the creation of intracellular microtubulins that are highly stable and dysfunctional, leading to cell death since normal tubule dynamics are disrupted, thereby prohibiting cell division. Based on this activity, paclitaxel is used as a chemotherapeutic agent for a wide variety of cancers, including ovarian, breast, colon, head, non-small cell lung carcinomas, and AIDS associated Kaposi sarcoma. Therapy with paclitaxel faces, as discussed above in general terms, two major problems: (1) it is in dire need of a tumor-targeted carrier as with any chemotherapeutic drug; and (2) it has extremely poor solubility in aqueous solutions. In the current approved formulations for paclitaxel used in the clinic, pacitaxel is dissolved in the highly toxic 1:1 blend of Cremophor EL (polyethoxylated castor oil) and ethanol.

Ongoing efforts in the field focus mostly on replacing the Cremophor EL/ethanol blend with more favorable vehicles, including carriers such as PEGylated liposomes. To date however, none has proved to be sufficiently satisfactory. While a better vehicle may be useful for overcoming the solubility problem, none of the efforts addresses the issue of tumor targeting. By contrast, the preferred embodiment of pacli-taxel encapsulated in the gagomer particles according to the present invention addresses both the targeting and solubility issues in a single carrier/delivery technology. This should reduce toxicity and adverse effects in patients and at the same time enhance treatment efficacy, resulting in significant improvements in clinical outcomes.

It has been previously found that water soluble drugs encapsulated in lipidated glycosaminoglycan particles were much more effective than the free drugs, particularly for cancer cells that have become drug resistant. It appears that the gagomers attach to the cancer cells and thus become depots of drugs which can enter the cells more quickly than they are excreted. These water soluble drugs thus have a toxic effect on cells despite the drug-resistance mechanisms that have been developed in cancer cells. It is expected that water insoluble or poorly water insoluble drugs encapsulated in lipidated glycosaminoglycan particles according to the present invention would also have an enhanced effect on cells compared to the free drug.

In addition to paclitaxel, other non-limiting examples of drugs/drug-models with poor aqueous solubility for encapsulation in gagomer particles are presented in Table 1 along with their therapeutic indications. A drug with an aqueous solubility of $\leq 30$ µg/ml is considered to be poorly water soluble or water insoluble. For purposes of the present invention, the term "drug" is intended to mean any agent which can affect the body therapeutically. Examples of therapeutic drugs include chemotherapeutics for cancer treatment, antibiotics for treating infections, antifungals for treating fungal infections, anti-inflammatories for treating inflammatory conditions, etc. As shown in the Examples hereinbelow, the lipid dilauryl phosphatidylethanolamine is preferred for encapsulating paclitaxel based on preparation, encapsulation efficiency and cytotoxicty. However, for some other drugs, it may turn out that dipalmitoyl phosphatidylethanolamine would be better and more preferred.

TABLE 1

Drugs/drug-models with poor aqueous solubility and therapeutic indications

| Water insoluble or poorly water soluble drug | Therapeutic indication |
| --- | --- |
| Pacitaxel (Taxol; TX) | Cancer/Oncology |
| Nile red (fluorescent probe) | Research tool |
| Etoposide (VP-16, Vepesid) | Cancer/Oncology |
| Cisplatin | Cancer/Oncology |
| Fluorouracil (5-FU) | Cancer/Oncology |
| Cyclosporin A | Transplantion/Immunosuppressant |
| Indomethacin | Antiinflammatory |
| Dexamethasone | Antiinflammatory |
| Nifedipine | Cardiac agents |
| Amphotericin B | Antibiotics Antimicrobial Antifungi |
| Neostatin | Antibiotics Antimicrobial Antifungi |
| Bethamethasone | Steroids |
| Cortisone | Steroids |

The gagomers used in the present invention are non-toxic microparticulate and nanoparticulate drug delivery systems, also referred to as MDDS and NDDS, respectively, that employ drug entrapping adhesive biopolymers. These carriers, when loaded with water insoluble or poorly water soluble drugs, improve clinical outcomes compared to the same drugs administered in their free form. Moreover, these gagomer particles have a number of other advantages over other particulate carriers, such as (1) good and sufficient retention in the circulation—the glycosaminoglycan component already has the hydrophilic outer shell found to delay opsonization and uptake by the RES, and (2) the bioadhesive nature of the glycosaminoglycan component endows the gagomer particles with the ability to adhere with high affinity to in vivo recognition sites and confers a measure of active targeting.

The drug-encapsulating gagomers of the present invention can be used in a pharmaceutical composition to treat a pathological condition in a subject in need thereof. The term "subject" as used herein is taken to include humans and other mammals such as cattle, sheep, pigs, goats, dogs, cats, rats, mice, etc., as well as animals including amphibians, birds, reptiles and fish.

Pathological conditions suitable for treatment with the drug encapsulated gagmomers of the present invention include any indication for which a water insoluble or poorly water soluble drug is used for treatment. Examples include, but are not limited to, cancer, bacterial and fungal infections including those secondary to trauma such as burns, infections caused by parasites or viruses, wound healing, inflammation, etc. Thus, the present invention also provides a method for treating a subject suffering from a pathological condition which involves administering to the subject an effective amount of the water insoluble or poorly water soluble drug encapsulated in the gagomer according to the present invention to treat the pathological condition. In the case of the preferred drug embodiment of pacilitaxel, the pathological condition is cancer.

The present invention is furthermore an improvement over current methods for delivering to a subject in need of treatment for a particular indication a water insoluble or poorly water soluble drug that is effective for treating that indication, the improvement being that the drug administered to the subject is encapsulated in gagomer particles.

Although naturally-occurring glycosaminoglycans are preferred in the gagomers used in the present invention in order to avoid problems with immunogenicity and toxicity, synthetic glycosaminoglycans can also be used, as well as natural, synthetic, or semisynthetic molecules, including but not limited to chondroitin, hyaluronic acid, glucuronic acid, iduronic acid, keratan sulfate, heparan sulfate, dermatin sulfate, and fragments, salts, and mixtures thereof. The term "glycosaminoglycan" as used herein further encompasses salts and free acids of glycosaminoglycan as well as glycosaminoglycans that have been chemically altered (but not partially hydrolyzed), yet retain their function. These modifications include, but are not limited to, esterification, sulfation, polysulfation, and methylation. Using hyaluronic acid (HA) as an example, its hyaluronate salts include sodium hyaluronate, potassium hyaluronate, magnesium hyaluronate, and calcium hyaluronate.

Natural sources of glycosaminoglycans include both plant and animal sources, i.e., beechwood trees and forms of animal cartilage, including shark cartilage, bovine trachea, whale septum, porcine nostrils, and mollusks such as *Perna canaliculus* and sea cucumber.

The glycosaminoglycans are used at sizes obtained when they are purified from their biological sources, and that have not been subjected to chemical and/or biological degradation. For example, for hyaluronic acid, this corresponds to a range of about $1 \times 10^5$ to about $1 \times 10^7$ daltons.

Pharmaceutical compositions containing the drug encapsulating gagomers according to the present invention can be administered by any convenient route, including parenteral, e.g., subcutaneous, intravenous, topical, intramuscular, intraperitoneal, transdermal, rectal, vaginal, intranasal or intraocular. Alternatively or concomitantly, administration may be by the oral route.

Parenteral administration can be by bolus injection or by gradual perfusion over time. Parenteral administration is generally characterized by injection, most typically subcutaneous, intramuscular or intravenous.

Topical formulations composed of the drug encapsulating gagomer particles of the present invention, penetration enhancers, and other biologically active drugs or medicaments may be applied in many ways. A liquid formation can be applied dropwise, from a suitable delivery device, to the appropriate area of skin or diseased skin or mucous membranes and rubbed in by hand or simply allowed to air dry. A suitable gelling agent can be added to the liquid formulation and the preparation can be applied to the appropriate area and rubbed in. For administration to wounds or burns, the gagomers may be incorporated into dosage forms such as oils, emulsions, and the like. Such preparations may be applied directly to the affected area in the form of lotions, creams, pastes, ointments, and the like.

Alternatively, the topical liquid formulation can be placed into a spray device and be delivered as a spray. This type of drug delivery device is particularly well suited for application to large areas of skin affected by dermal pathologies, to highly sensitive skin or to the nasal or oral cavities. Optionally, the gagomers may be administered in the form of an ointment or transdermal patch.

Oral routes of administration are understood to include buccal and sublingual routes of administration.

The gagomers of the present invention may also be administered by other routes which optimize uptake by the mucosa. For example, vaginal (especially in the case of treating vaginal pathologies), rectal and intranasal routes are the preferred routes of administration. Furthermore, the gagomers are particularly suited for delivery through mucosal tissue or epithelia. If administered intranasally, the gagomers will typically be administered in an aerosol form, or in the form of drops. This may be especially useful for treating lung pathologies. Suitable formulations can be found in *Remington's Pharmaceutical Sciences,* 16th and 18th Eds., Mack Publishing, Easton, Pa. (1980 and 1990), and *Introduction to Pharmaceutical Dosage Forms,* 4th Edition, Lea & Febiger, Philadelphia (1985), each of which is incorporated herein by reference.

Depending on the intended mode of administration, the compositions used may be in the form of solid, semi-solid or liquid dosage forms, such as for example, tablets, suppositories, pills, capsules, powders, liquids, suspensions, or the like, preferably in unit dosage forms suitable for single administration of precise dosages. The pharmaceutical compositions contains the drug encapsulating gagomer particles of the present invention and a pharmaceutically acceptable diluent, carrier, excipient, adjuvant, or auxiliary agent. It is preferred that the pharmaceutically acceptable carrier be one which is chemically inert to the active compounds and which has no detrimental side effects or toxicity under the conditions of use. The choice of carrier is determined partly by the particular active ingredient, as well as by the particular method used to administer the composition. Accordingly, there are a wide variety of suitable formulations of the pharmaceutical compositions of the present invention.

Suitable excipients are, in particular, fillers such as saccharides (e.g., lactose or sucrose, mannitol, sorbitol, etc.) cellulose preparations and/or calcium phosphates (e.g., tricalcium phosphate, calcium hydrogen phosphate, etc.) as well as binders such as starch paste using, for example, maize starch, wheat starch, rice starch, potato starch, gelatin, tragacanth, methylcellulose, hydroxypropylmethylcellulose, sodium carboxymethylcellulose, and/or polyvinyl pyrrolidine.

Injectable formulations for parenteral administration can be prepared as liquid suspensions, solid forms suitable for solution or suspension in liquid prior to injection, or as emulsions. Suitable excipients are, for example, water, saline, dextrose, glycerol, ethanol or the like. In addition, if desired, the pharmaceutical composition to be administered may also contain minor amounts of non-toxic auxiliary agents such as wetting or emulsifying agents, pH buffering agents and the like, such as for example, sodium acetate, sorbitan monolaurate, triethanolamine oleate, etc.

Aqueous injection suspensions may also contain substances that increase the viscosity of the suspension, including, for example, sodium carboxymethylcellulose, sorbitol, and/or dextran. Optionally, the suspension may also contain stabilizers.

The parenteral formulations can be present in unit dose or multiple dose sealed containers, such as ampules and vials, and can be stored in a freeze-dried (lyophilized) condition requiring only the addition of the sterile liquid carrier, e.g., water, for injections immediately prior to use. Extemporaneous injection suspensions can be prepared from sterile powders, granules, and tablets of the kind previously described.

For oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium crosscarmellose, glucose, gelatin, sucrose, magnesium carbonate, and the like. Such compositions include suspensions, tablets, dispersible tablets, pills, capsules, powders, sustained release formulations and the like. Formulations suitable for oral administration can consists of liquid suspensions such as effective amounts of the drug encapsulating gagomer particles suspended in diluents such as water, saline, or orange juice; sachets, lozenges, and troches, each containing a predetermined amount of the active ingredient as solids or granules; powders, suspensions in an appropriate liquid; and suitable emulsions. Liquid formulations may include diluents such as water and alcohols, e.g., ethanol, benzyl alcohol, and the polyethylene alcohols, either with or without the addition of a pharmaceutically acceptable surfactant, suspending agents, or emulsifying agents.

When the composition is a pill or tablet, it will contain, along with the active ingredient, a diluent such as lactose, sucrose, dicalcium phosphate, or the like; a lubricant such as magnesium stearate or the like; and a binder such as starch, gum acacia, gelatin, polyvinylpyrolidine, cellulose and derivatives thereof, and the like.

Tablet forms can include one or more of lactose, sucrose, mannitol, corn starch, potato starch, alginic acid, microcrystalline cellulose, acacia, gelatin, guar gum, colloidal silicon dioxide, crosscarmellose sodium, talc, magnesium stearate, calcium stearate, zinc stearate, stearic acid, preservatives, flavoring agents, pharmaceutically acceptable disintegrating agents, moistening agents, and pharmacologically compatible carriers.

Capsule forms can be of the ordinary hard- or soft-shelled gelatin type containing, for example, surfactants, lubricant, and inert fillers, such as lactose, sucrose, calcium phosphate, and corn starch.

Lozenge forms can contain the drug encapsulating gagomer particles in a carrier, usually sucrose and acacia or tragacanth, as well as pastilles comprising the active ingredient in an inert base such as gelatin or glycerin, or sucrose and acacia.

In determining the dosages of the gagomer particles to be administered, the dosage and frequency of administration is selected in relation to the pharmacological properties of the specific active ingredients. Normally, at least three dosage levels should be used. In toxicity studies in general, the highest dose should reach a toxic level but be sublethal for most animals in the group. If possible, the lowest dose should induce a biologically demonstrable effect. These studies should be performed in parallel for each compound selected.

Additionally, the $ED_{50}$ (effective dose for 50% of the test population) level of the active ingredient (drug encapsulating gagomer particles) in question should be one of the dosage levels selected, and the other two selected to reach a toxic level. The lowest dose is that dose which does not exhibit a biologically demonstrable effect. The toxicology tests should be repeated using appropriate new doses calculated on the basis of the results obtained.

Young, healthy mice or rats belonging to a well-defined strain are the first choice of species, and the first studies generally use the preferred route of administration. Control groups given a placebo or not treated are included in the tests. Tests for general toxicity, as outlined above, should normally be repeated in another non-rodent species, e.g., a rabbit or dog. Studies may also be repeated using alternate routes of administration.

Single dose toxicity tests should be conducted in such a way that signs of acute toxicity are revealed and the mode of death determined. The dosage to be administered is calculated on the basis of the results obtained in the above-mentioned toxicity tests. It may be desired not to continue studying all of the initially selected compounds.

Data on single dose toxicity, e.g., $LD_{50}$, the dosage at which 50% of the experimental animals die, is to be expressed in units of weight or volume per kg of body weight and should generally be furnished for at least two species with different modes of administration. In addition to the $LD_{50}$ value in rodents, it is desirable to determine the highest tolerated dose and/or lowest lethal dose for other species, i.e., dog and rabbit.

When a suitable and presumably safe dosage level has been established as outlined above, studies on the chronic toxicity of the drug encapsulating gagomer particles, its effect on reproduction, and potential mutagenicity may also be required in order to ensure that the calculated appropriate dosage range will be safe, also with regard to these hazards.

Pharmacological animal studies on pharmacokinetics revealing, e.g., absorption, distribution, biotransformation, and excretion of the active ingredient and metabolites are then performed. Using the results obtained, studies on human pharmacology are then designed.

Studies of the pharmacodynamics and pharmacokinetics of the compounds in humans should be performed in healthy subjects using the routes of administration intended for clinical use, and can be repeated in patients. The dose-response relationship when different doses are given, or when several types of conjugates or combinations of conjugates and free compounds are given, should be studied in order to elucidate the dose-response relationship (dose vs. plasma concentration vs. effect), the therapeutic range, and the optimum dose interval. Also, studies on time-effect relationship, e.g., studies into the time-course of the effect and studies on different organs in order to elucidate the desired and undesired pharmacological effects of the drug, in particular on other vital organ systems, should be performed.

The compounds of the present invention are then ready for clinical trials to compare the efficacy of the compounds to existing therapy. A dose-response relationship to therapeutic effect and side effects can be more finely established at this point.

The amount of the drug encapsulating gagomer particles of the present invention to be administered to any given patient must be determined empirically, and will differ depending upon the condition of the patients. Relatively small amounts of the drug encapsulating gagomer particles can be administered at first, with steadily increasing dosages if no adverse effects are noted. Of course, the maximum safe toxicity dosage as determined in routine animal toxicity tests should never be exceeded.

Compositions within the scope of the present invention include all compositions wherein the gagomers encapsulating the water insoluble or poorly water soluble drug is contained in an amount effective to achieve its intended purpose. While individual needs vary, determination of optimal ranges of effective amounts of each compound is within the skill of the art. The dosage administered will depend upon the age, health, and weight of the individual recipient thereof as well as upon the nature of any concurrent treatment and the effect desired. Typical dosages include 0.01 to 100 mg/kg body weight. The preferred dosages are in the range of about 0.1 to 100 mg/kg body weight. The most preferred dosages are in the range of about 1 to 50 mg/kg body weight.

Preparation of the gagomers with drug entrapment is simple and cost-effective. These drug encapsulating gagomer particles act as sustained release drug depots, with half-lives in the range of 19-35 hours for the efflux of antibiotics and chemotherapeutics. These properties of the gagomer particles, together with their bioadhesive nature, provide these drug carriers the ability to perform as site-adherent, site-retained, sustained release drug depots for systemic, including oral, topical, and regional, including intranasal, administrations.

The principles of gagomer preparation are to dissolve the lipid in an organic solvent and evaporate it to dryness in a manner that forms a thin lipid film, which is then hydrated in a basic buffer, usually borate buffer at pH9. Alternatively, the lipid can be hydrated directly in an appropriate basic buffer at a temperature above the lipid's Tm. The glycosaminoglycan is dissolved separately in an acidic aqueous phase and activated by a water-soluble coupling agent such as a carbodiimide. The hydrated lipid film and the aqueous solution of the activated glycosaminoglycan are brought together and the system is maintained in a basic pH buffer for the covalent bonding to take place.

Two basic types of gagomers may be synthesized: low lipid to glycosaminoglycan ratio (1:1, w/w), denoted LLG, and high ratio of lipid to glycosaminoglycan (5:1 to 20:1, w/w), denoted HLG. By changing specific steps in the preparation, the outcome can be directed to form micro- or nanoparticles.

The gagomers formed by the procedures of the present invention may be lyophilized (freeze-dried), with or without drug, and rehydrated with water alone or rehydrated with an aqueous solution of a drug of interest.

Unlike other particulate carriers such as liposomes, there is no need to add protective agents (cryoprotectants such as sugars) to the gagomers prior to lyophilization, in order to enhance long-term storage and stability of the preparations. The gagomers have intrinsic cryoprotection provided by the hyaluronan (hyaluronic acid).

Following rehydration, the preparation may be heated. Once the gagomers have been lyophilized, they can be stored for extended periods of time until they are to be used. The appropriate temperature for storage will depend on the lipid formulation of the gagomers and temperature sensitivity of encapsulated materials.

When the lyophilized gagomers are to be used, rehydration is accomplished by simply adding an aqueous solution, such as distilled water or an appropriate buffer, to the gagomers and allowing them to rehydrate. This rehydration can be performed at room temperature or at other temperatures appropriate to the composition of the gagomers and their internal contents.

The gagomers of the present invention, lipidated glycosaminoglycans, are preferably prepared by covalently binding a lipid having at least one primary amino group, preferably a phospholipid, more preferably a phosphatidylethanolamine, and most preferably dilauryl or dipalmitoyl phosphatidylethanolamine, to a carboxylic acid-containing glycosaminoglycan, preferably hyaluronic acid (HA), by the following method:

(1) separately dissolving a lipid and a water insoluble or poorly water soluble active ingredient in an organic solvent;

(2) combining the dissolved lipid and dissolved water insoluble or poorly water soluble active ingredient together into a combined solution;

(3) evaporating the combined solution to dryness and dispersing as a suspension in a basic borate buffer;

(4) mixing and incubating the dispersed suspension with a solution of glycosaminoglycan, activated by pre-incubation with a coupling agent, to form lipidated glycosaminoglycan particles encapsulating the water insoluble or poorly water soluble active ingredient; and (5) fractionating by successive centrifugation to enrich for lipidated glycosaminoglycan particles. The fractionated and enriched lipidated glycosaminoglycan particles can be further optionally lyophilized.

Alternatively, the lipidated gagomers can be prepared prior to encapsulating the drug/active ingredient by the following method:

(a) A reaction vessel is provided in which the lipid is spread in a thin layer on the vessel bottom and walls. This can be effected by dissolving the lipid in an organic solvent and evaporating the lipid to dryness under low pressure in a rotary evaporator.

(b) The glycosaminoglycan is activated by pre-incubation in acidic pH with a crosslinker.

(c) The activated glycosaminoglycan is added to the reaction vessel.

(d) The reaction mixture of the lipid and activated glycosaminoglycan is buffered to a basic pH in a range of 8.6-9.0.

(e) The buffered reaction mixtures are incubated, with continuous shaking, for a period of time sufficient for the lipidated glycosaminoglycan to form, such as overnight at 37° C. Since the lipidated gags are designed to be used in vivo, they should be stable at about 37° C. While higher temperatures can be used for lipidation, lipids undergo physical changes with rising temperatures, generally about 62° C. Therefore, the lipidation preferably is conducted at temperatures from about 30-40° C.

(f) The lipidated glycosaminoglycan is buffered to a neutral pH and other ions and water-soluble additives are added according to need in order to elevate the ionic strength to physiological levels with ions or salts present in biological fluids (such as NaCl, KCl, $Ca^{2+}$ and $Mg^{2+}$).

(g) The particles are fractionated by successive centrifugations, each run at 4° C., for 40 minutes at the g force of $1.6 \times 10^5$, as follows: The pellet after 3 runs is the microparticle-enriched fraction, the supernatant of the microparticle enriched fraction subjected to 3 additional runs is the nanoparticle-enriched fraction.

(h) The resulting lipidated glycosaminoglycan is lyophilized.

(i) A stock solution of the water insoluble or poorly water soluble active ingredient is prepared in an organic solvent such as DMSO or ethanol. A working solution is then prepared by diluting the stock solution into water, so that the concentration of the organic solvent is ≦1%. This working solution is then used to rehydrate the lyophilized gagomer powder.

Turbidity studies, following light scattering in a spectrophotometer, may be conducted for equal concentrations of soluble hyaluronic acid and of a gagomer prepared from hyaluronic acid and phosphatidylethanolamine to gain insight into whether the synthesis actually yields particulate matter. As expected, over the concentration range tested free hyaluronic acid is soluble, and its solutions do not scatter light. In contrast, the gagomer-containing samples are turbid, the light scattering increasing with the gagomer concentration, making it clear that the biopolymer is an insoluble material.

The lipidated glycosaminoglycan particles are preferably made without any encapsulated materials and then lyophilized to form a powder. The powdered glycosaminoglycan particles are then mixed with a powder of the material to be encapsulated. Alternatively, the powdered glycosaminoglycan particles are reconstituted by mixing with a solution of the material to be encapsulated in an organic solvent, which organic solvent is preferably ethanol. Once the mixture is reconstituted, the particles will have captured the material that was mixed in. Thus, small water-insoluble or poorly water soluble molecules, such as antibiotics and chemotherapeutic drugs, as well as large molecules, can be encapsulated with this technique.

The particles of the present invention are prepared by reacting at least one glycosaminoglycan in the long form, i.e., the gag has not been sliced up into smaller sizes. All glycosaminoglycans, except hyaluronic acid, are naturally in the form of a protein moiety bound covalently to a poly-saccharide moiety. Methods for hydrolyzing the protein-sugar bond, both chemically and enzymatically, are well known to those skilled in the art. In addition, some commercial products are available in which the protein moiety has already been removed.

The glycosaminoglycan polymer is reacted with a lipid which has at least one primary amino group to cross-link the carboxylic residue of the glycosaminoglycan to a primary amine in the lipid. Once this reaction occurs, thermodynamic stability causes the lipids to interact with one another so as to pull the product into a sphere having the glycosaminoglycan on the outside and the lipids on the inside. Self-assembly of the lipid molecules is a critical force in obtaining the gagomer particles. These particles are used to encapsulate the water insoluble or poorly water soluble drugs/active ingredients in the interior of the particles.

In one embodiment of the present invention, the protein part of the glycosaminoglycan is removed and only the sugar backbone is reacted with the lipids.

It is known in the art to attach hyaluronic acid to the outside of liposomes for targeting or for making the liposomes more bioadhesive. In the instant invention, there is no liposome; rather, lipid molecules are attached covalently to hyaluronic acid.

In another embodiment of the present invention, other molecules may be attached first to the glycosaminoglycan, which is then reacted with lipids. The particles produced have theseother molecules appearing on the outside of the particles. These other molecules may be, for example, antibodies, folate, porphyrins, or lectins, and may be used for targeting.

Having now generally described the invention, the same will be more readily understood through reference to the following examples which are provided by way of illustration and are not intended to be limiting of the present invention.

Example 1

Preparation of Paclitaxel-Loaded Gagomers

Initial Drug Dissolution in DMSO, Followed by Extensive Dilution into Water (Referred to as the Via-DMSO Method)

Lyophilized drug-free gagomer powders were prepared as follows:
Steps (1) and (2) Below were Run in Parallel:
(1) Hyaluronan (HA) was dissolved in water, to a concentration of 2 mg/ml. EDC was added to the solution at a ratio of 20 mg/mg HA, the pH was adjusted to 4.0 by titration with HCl (1M), and the system was incubated for 2 hours, at 37° C., in a shaker.
(2) 60 mg of dipalmitoyl phosphatidylethanolamine (DPPE) were dissolved in chloroform:methanol (3:1, v/v) to a concentration of 1.5 mg/ml and the solution was evaporated to complete dryness under low pressure in a rotary evaporator, until a dry uniform film was obtained. Thereafter, 10 ml 0.1M Borate buffer, pH 9.0, was added to the dried lipid, the suspension vigorously agitated for several minutes, then incubated for 2 hours at 37° C. in a shaker to create a uniform lipid dispersion.
(3) The solution of activated HA and the basic suspension of the PE were mixed in a 1:1 HA:lipid weight ratio, and incubated overnight at 37° C. in a shaker.
(4) The reaction mixture from (3) was centrifuged in a ultra-centrifuge for 40 minutes at a g force of 160,000, and 4° C. The supernatant was discarded, and the pellet was subjected to 4 cycles of washings as follows: pellet resuspension in phosphate buffered saline (PBS), pH 7.2, recentrifuged under the conditions listed above. The supernatant was discarded, the pellet was resuspended in PBS and so forth. The final pellet was suspended in PBS to a desired volume (usually that of system (3)).
(5) The gagomer suspension was dispensed into lyophilization mini bottles of 1 ml, and lyophilized as follows: 2 hours freezing at −80° C., with lyophilization over-night (ambient temperature, condenser temperature LT−50° C., pressure 0.055 hPa. The gagomer powder was stored frozen (−18° C.) until use.

In this example and in all subsequent examples, the gagomer concentration will be defined by its phosphatidylethanolamine (PE) content.

Stock solutions of paclitaxel in DMSO were prepared in the drug concentration range of 40 mM. Working paclitaxel solutions were prepared by dilution of these stock solutions in water to the concentration range of 170-625 µg/ml and final DMSO concentrations were <1%. A given working solution was immediately mixed with a selected quantity of the gagomer powder to final gagomer concentrations in the range of 0.16-5 mg PE/ml. The mixtures were incubated for 2 hours in a shaker bath at 37° C. Paclitaxel was assayed by inclusion of a trace of $^3$H-paclitaxel in the formulation.

Efficiency of drug encapsulation is defined as the fraction of total drug in the system that is encapsulated within the carrier particles. Paclitaxel encapsulation efficiency was determined by the "thermodynamic method", as follows. Paclitaxel-gagomer formulations were subjected to ultra high speed centrifugation (40 minutes, 4° C., g force of 175000). The supernatant (which contains unencapsulated drug) was separated from the pellet (which contains the drug-encapsulating gagomers). The pellet was re-suspended in drug-free buffer to the original volume. The paclitaxel concentration was determined in the original formulation before the separation, in the supernatant and in the resuspended pellet, and these data were used to determine the efficiency of encapsulation. As shown in FIG. 1, paclitaxel encapsulation efficiency in these preparations was very high, 96(±2)%, and was not sensitive to gagomer concentration.

Example 2

Preparation of Paclitaxel-Loaded Gagomers

Initial Drug Dissolution in Ethanol, Followed by Extensive Dilution into Water (Referred to as the Via-Ethanol Method)

Figure 2:
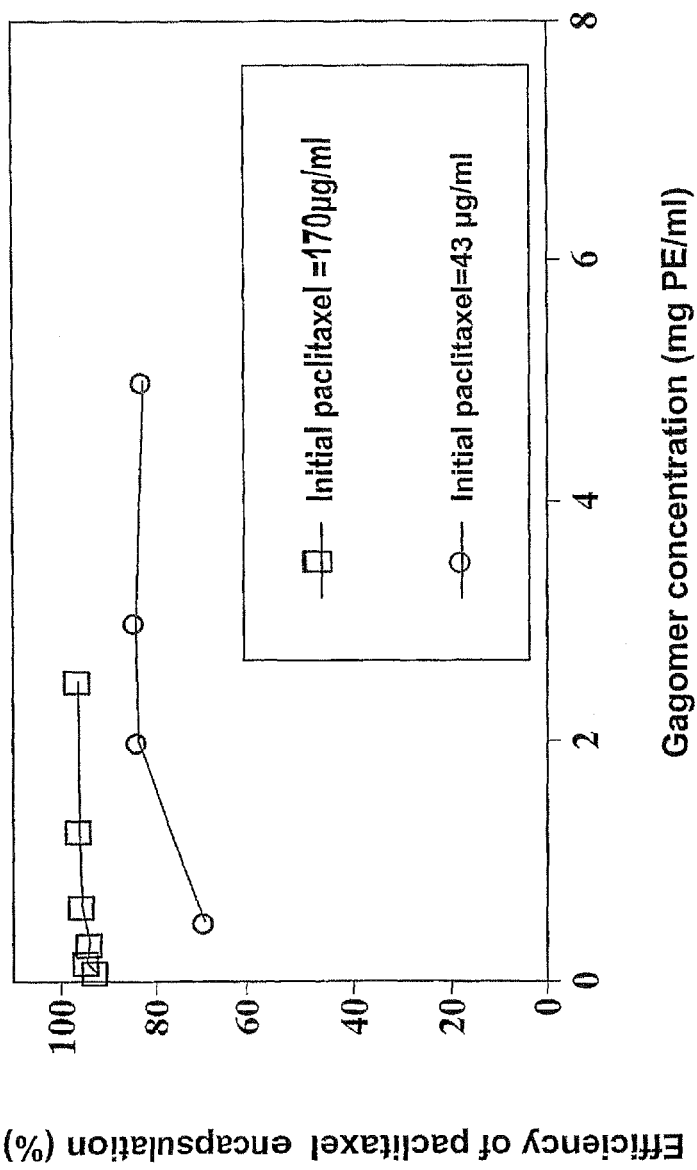
FIG. 2 is a graph showing the efficiency of paclitaxel encapsulation in gagomers, in the via-ethanol method, as a function of gagomer concentration (in units of mg PE/ml). The points are the experimental data obtained at different initial drug concentration as listed. The solid lines are non-theoretical, drawn to emphasize the trends of the data.

Paclitaxel-gagomer formulations were prepared similar to those described in Example 1, but with the following distinction: ethanol was used as the solvent for the stock solution instead of DMSO. Working paclitaxel concentrations were in the range of 43-170 μg/ml and final ethanol concentrations were <1%. As shown in FIG. 2, high encapsulation efficiencies, 80(±6) % and 95(±1) % for the high and low taxol concentrations, respectively, were also obtained by this approach with slight or no dependence on gagomer concentration within the range tested.

Example 3

Preparation of Paclitaxel-Loaded Gagomers

Initial Drug Dissolution in Ethanol, Followed by Addition to the Organic PE Solution (Referred to as the Via-PE Method)

In this approach, paclitaxel was introduced in the course of gagomer preparation, at the stage in which the PE is dissolved in an organic solvent system. Paclitaxel was dissolved in ethanol and added to the PE solution in chloroform:methanol 3:1 v/v, at room temperature (i.e., step 2 in Example 1 above). From this point on, gagomer preparation proceeded as described in Example 1, except that step 5 (lyophilization) was omitted.

Figure 3:
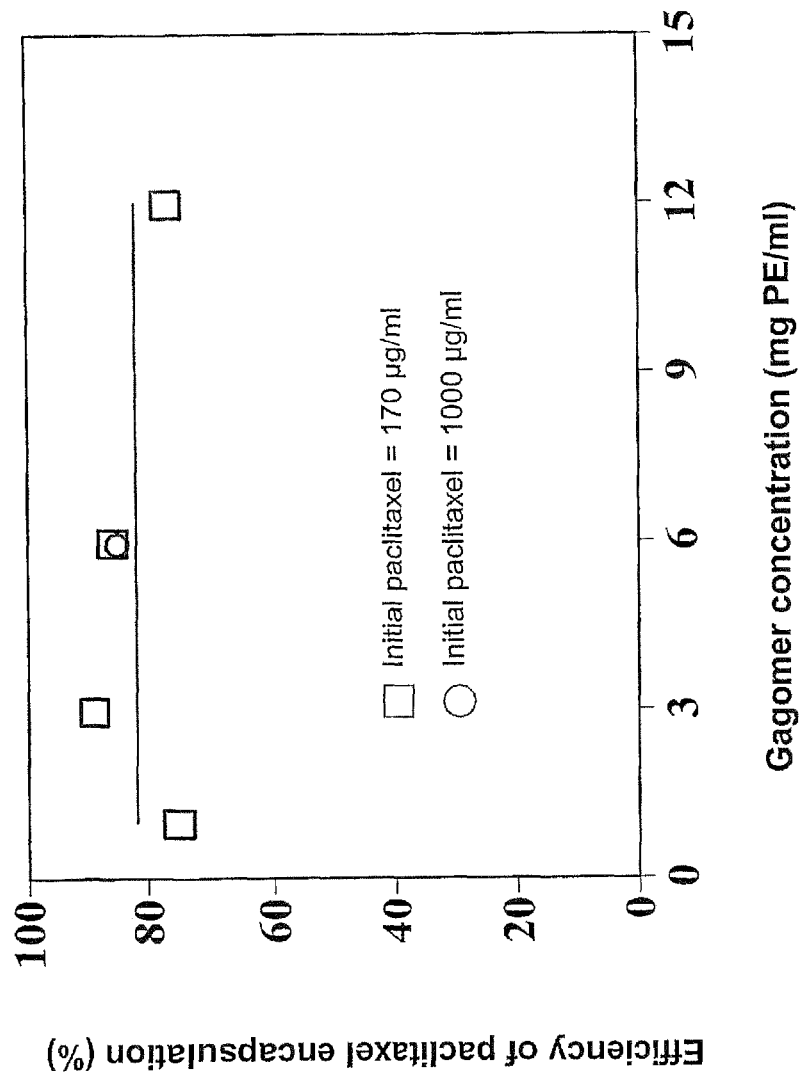
FIG. 3 is a graph showing the efficiency of paclitaxel encapsulation in gagomers, carrier preparation and drug encapsulation in the via-PE method, as a function of gagomer concentration (in units of mg PE/ml). The points are the experimental data obtained at different initial drug concentration as listed. The solid line and the error bars are the average encapsulation efficiency and sd, for all data points.

Paclitaxel final concentrations in the formulation were 0.2-1.2 mM. As shown in FIG. 3, this method also yields high encapsulation efficiencies, 82(±5) %, with the advantage that this approach allows encapsulating higher drug doses than the approaches of Examples 1 and 2. This latter point is emphasized by the comparison shown in Table 2, for the systems in which paclitaxel was dissolved in ethanol. Although the encapsulation efficiency is relatively lower than in the "via PE" method, it allows use of much higher drug doses. Consequently, the encapsulated drug dose in the preferred method (i.e., via-PE) is 5 fold higher.

TABLE 2

| | Paclitaxel loading stocks | | |
|---|---|---|---|
| Method of drug encapsulation | Highest Paclitaxel Dose used (μg/ml) | Encapsulation efficiency (%) | Encapsulated Paclitaxel dose (μg/ml) |
| Via ethanol | 170 | 96 | 163 |
| Via PE | 1000 | 84 | 840 |

Example 4

Relationship of Encapsulation Efficiency and Paclitaxel Loading

Figure 4:
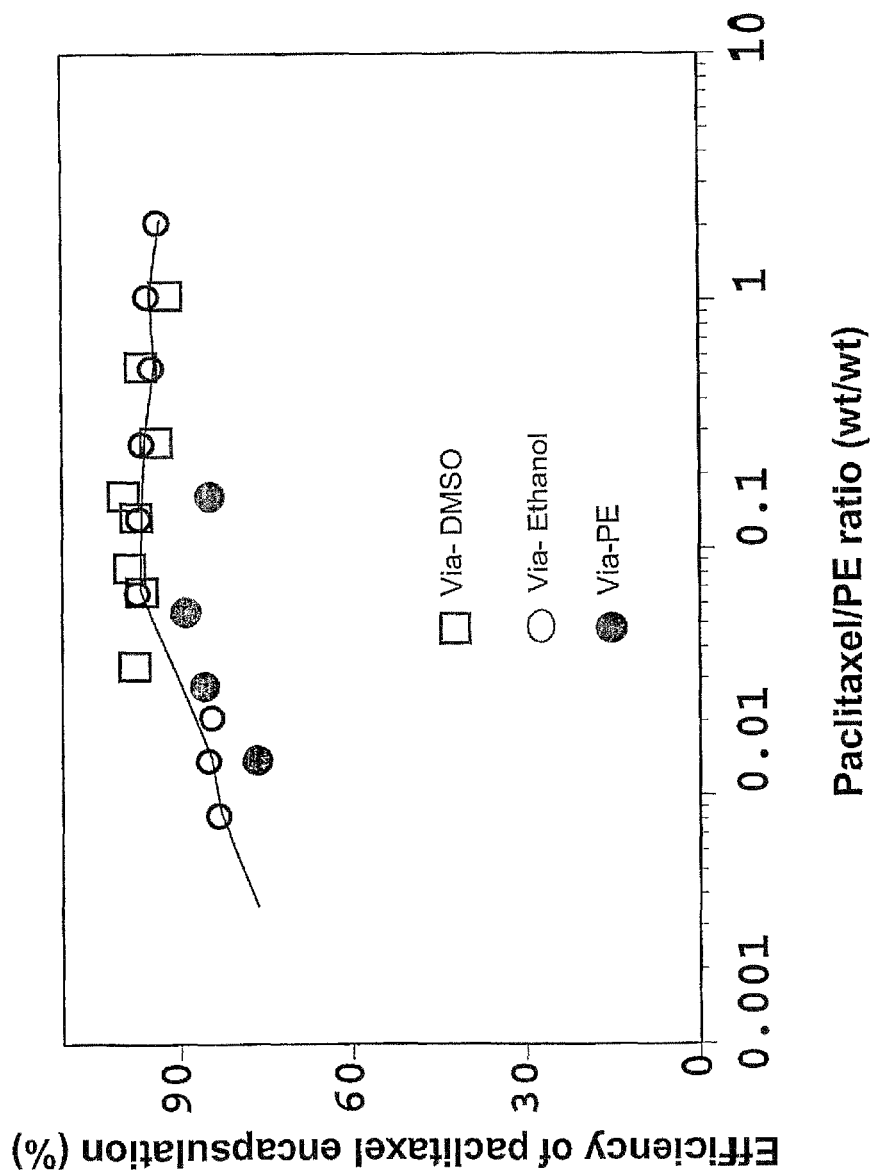
FIG. 4 is a graph showing comparisons of the efficiency of paclitaxel encapsulation in the three types of formulations (i.e., via-DMSO, via-ethanol and via-PE) as a function of the drug/gagomer ratio. Abbreviations used: TX—paclitaxel; GAG—gagomers; HA—hyaluronan; PE—phosphatidylethanolamine. The points are experimental, with the symbols as follows: open box: via DMSO; open circle: via ethanol; solid circle: via PE. The solid curve is non-theoretical, drawn to emphasize the trend of the data.

Encapsulation efficiencies for all three methods described in Examples 1-3 above were compared vs. the loading level (paclitaxel/PE, wt/wt). As seen in FIG. 4, there is good agreement between the three encapsulation methods over a wide range of paclitaxel loadings.

Example 5

Stability in Serum

A comprehensive stability profile of paclitaxel-gagomer formulations in serum requires: (1) Retention of particle integrity that can be monitored by following, independently, the fate of the two components—hyaluronan and PE and (2) retention of the loaded drug within the particle.

To evaluate serum stability of the paclitaxel-gagomer formulations, samples were incubated up to 24 hours in 50% human serum, at 37° C. To gain more insight into the serum effects on particle integrity and its sensitivity to the presence of paclitaxel, similar studies were conducted with drug-free gagomers. Aliquots were withdrawn from the reaction mixtures at selected time points within the entire duration of the experiment, and subjected to separation by centrifugation. Centrifugation conditions and details were similar to those disclosed in Example 1 for the thermodynamic method of determining encapsulation efficiency.

Figure 5:
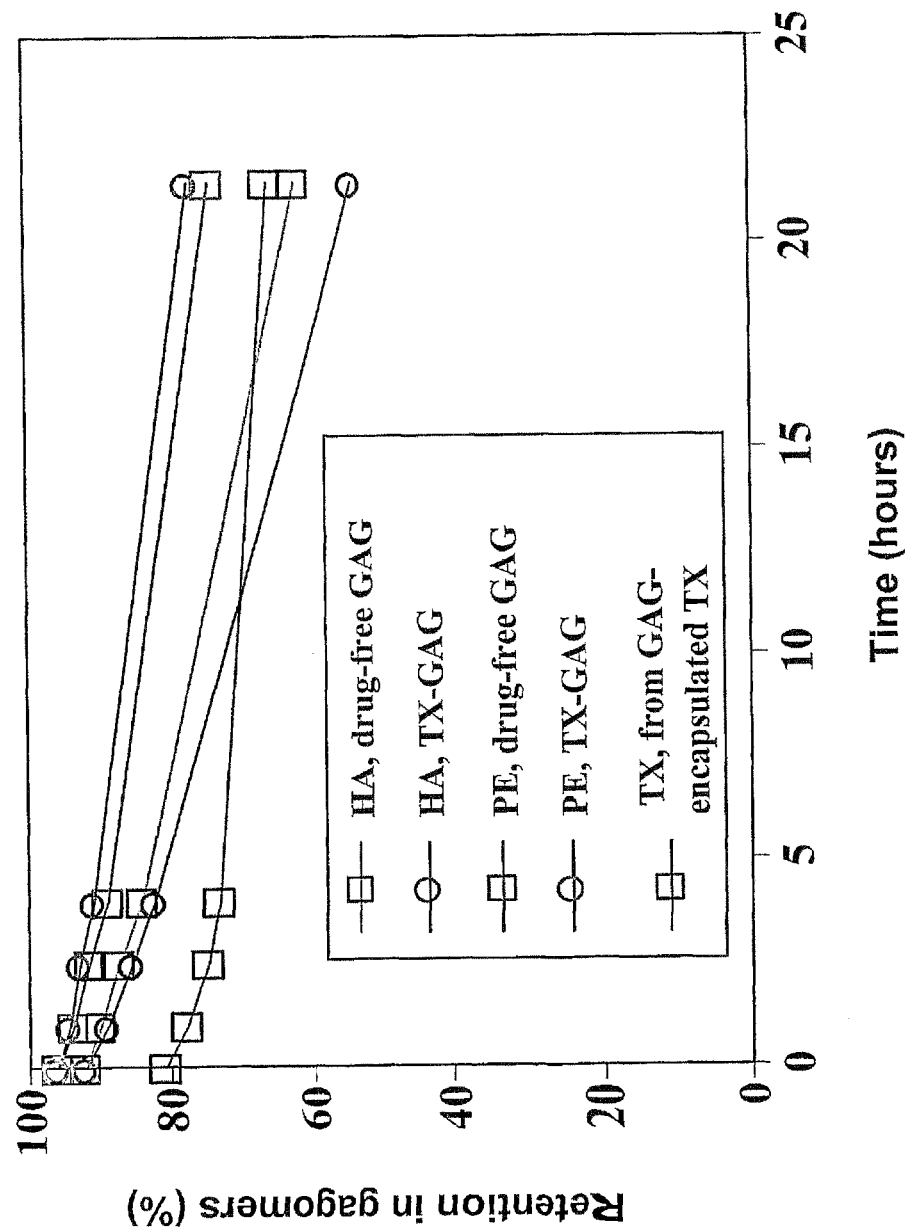
FIG. 5 is a graph showing the stability of drug-free gagomers and of paclitaxel-encapsulating gagomers (prepared via the ethanol method) in 50% human serum and at 37° C. as a function of time. Separately monitoring HA concentration in gagomers, PE concentration in gagomers, level of drug encapsulation. Drug-free and paclitaxel-encapsulating gagomers were (TX-GAG) prepared by the via-ethanol method. The points are experimental and the specific symbols for each tested variable are listed. The solid curves are non-theoretical, drawn to emphasize the trends of the data.

The pellets containing intact gagomers and their encapsulated drug were resuspended in PBS. Hyaluronan (HA), PE and paclitaxel were assayed in the withdrawn aliquot before centrifugation, in the supernatant and in the resuspended pellet, making use of the following trace labels: FITC-labeled HA (F-HA), $^{14}$C-PE, and, where relevant, $^3$H-paclitaxel. The results are summarized in FIG. 5.

The data show quite clearly, for both drug-free and drug-loaded test systems, that the majority of hyaluronan, independently of PE, are retained in the pellet. This retention is furthermore at the same level for both components over most of the time span. These findings allow the conclusion that there is good particle stability in serum. Similar retention of the encapsulated drug further substantiates this conclusion.

Taking all the data together makes it clear that not only are the gagomers stable in serum, the encapsulated drug is not lost from intact particles, and its presence does not impair particle stability in serum.

Example 6

Paclitaxel Efflux from Intact Gagomers

Figure 6:
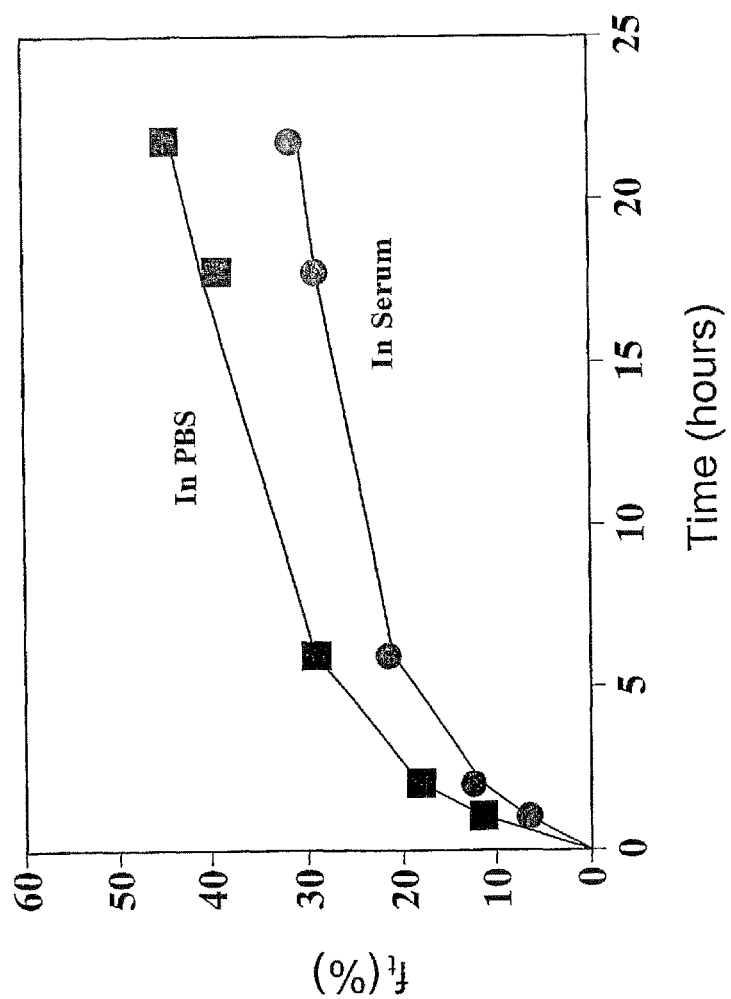
FIG. 6 is a graph showing the kinetics of paclitaxel efflux from gagomers prepared with the via ethanol method, in PBS and, separately, in 50% serum, under unidirectional flux (sink) conditions. The dependant variable $f_t$ is fraction of total drug released from the formulation at time=t. The points are the experimental data. The solid curves are the theoretical expectations drawn according to equation (1) and the kinetic parameters listed in the footnotes of Table 3.

The efflux of paclitaxel from the gagomers was studied in both PBS and in 50% human serum under unidirectional flux (sink) conditions, using the dialysis approach essentially as described in WO 03/015755 and Margalit et al. (1991). A trace of $^3$H-paclitaxel was included in the preparation to assay paclitaxel that was released from the dialysis sac at each time point, as well as the paclitaxel in the gagomers at time=0 and at the end of the experiment. Data processing and analysis was performed according to the procedures previously developed in the laboratory of the present inventors (WO 03/015755; Margalit et al., 1991) and found to fit the case of two independent drug pools at time=0, one of encapsulated drug, the other of un-encapsulated drug. The results are shown in FIG. 6 and Table 3. This type of data analysis reconstructs the distribution of drug between the gagomers and the external medium at time=0, and constitutes therefore another approach to determining encapsulation efficiency, independent of the thermodynamic approach disclosed in Example 1.

TABLE 3

Parameters of paclitaxel efflux from gagomers in PBS and in serum

| Gagomer Concentration (mg PE/ml) | Medium | $f_2^{(2)}$ (%) | $k_1$ (hours$^{-1}$) | Efflux of encapsulated Paclitaxel | |
|---|---|---|---|---|---|
| | | | | $k_2$ (hours$^{-1}$) | $\tau_{1/2}$ (hours) |
| 6 | PBS | 76 ± 2 | 0.54 ± 0.09 | 0.014 ± 0.002 | 49 |
| 6 | Serum$^{(1)}$ | 79 ± 2 | 0.34 ± 0.09 | 0.006 ± 0.002 | 115 |

$^{(1)}$50% human serum in PBS
$^{(2)}$Equation (1): $f_t = (100 - f_2)(1 - e^{-k_1 t}) + f_2(1 - e^{-k_2 t})$
$f_t$—fraction of total drug released from the formulation at time = t
$f_2$: fraction of gagomer-encapsulated drug at time = 0
$k_1$: rate constant of efflux for the unencapsulated drug
$k_2$: rate constant of efflux for the encapsulated drug Each data set in FIG. 6 shows the combined accumulation of both encapsulated and un-encapsulated drug in the dialysates, and it is clearly seen that efflux in the presence of serum is slower than in PBS. As can be seen in Table 3, concomitant with the data and conclusions of Example 4 above, high serum stability is retained—the $f_2$ (the encapsulation level) values are quite similar in serum and in PBS. In both media, the paclitaxel-gagomer formulations perform as sustained-release drug depots, a trait highly-desirable in drug carriers.

Interestingly, both rate constants are reduced when serum is present within the dialysis sac. Serum components most relevant for the present case—efflux of a lipophilic drug—are albumin and lipoproteins, both of which remain within the sac throughout the experiment (the membrane cutoff is 12000-14000 Da). As discussed in detail in Margalit et al. (1991), efflux of unencapsulated drug and of the encapsulated drug from the dialysis sac to the dialysate is each an independent multi-step process with a single rate limiting step, in which the drug diffuses from its original pool through a series of intermediate pool, ending in the dialysate. This same pattern—a single rate limiting step for diffusion from each original drug pool—also holds in the present cases of paclitaxel, and the serum vs. PBS differences of the rate constants imply minor changes in the environment of the rate-limiting drug pools.

Example 7

Cytotoxicity In Vitro

Cytotoxicity of paclitaxel and of gagomer-encapsulated paclitaxel was evaluated over a matrix of drug-gagomer formulations (see Examples 1, 2 and 3), cell lines and treatment protocols, for the drug concentration range spanning from 1 nM to 100 μM.

Twenty four hours prior to an experiment, cells of the desired line were seeded onto 96-well multiwell culture plates at densities in the range of 5×10$^3$ cells/well. The experiments were initiated on sub-confluent monolayers. Upon initiation of an experiment, treatment media was added, as listed in Table 4. Two protocols were used:

(I) Short protocol. The cells were incubated with the treatment media for 4 hours, at the end of which the treatment media was aspirated, the cells washed and incubated for 44 hours in drug-free serum-supplemented cell growth media. Termination was 48 hours from start.

(II) Long protocol: the cells were incubated in the treatment media for 48 hours. Upon termination, in either protocol, cell viability was determined in each well using either the MTT or the SRB assay method.

TABLE 4

Composition of treatment media for in vitro evaluation of paclitaxel-gagomer cytotoxicity.

| Treatment group | Composition of treatment media |
|---|---|
| 1 | Drug-free serum-supplemented cell growth media |
| 2 | Free paclitaxel diluted in serum-supplemented cell growth media |
| 3 | Paclitaxel-gagomers suspended in serum-supplemented cell growth media |
| 4 | Drug-free gagomers suspended in serum-supplemented cell growth media |

The rationale for the two protocols, the long and the short, is as follows: The long protocol is the traditional one used for in vitro comparisons of cytotoxicity among different drug formulations. The cells are incubated with the treatment formulations for periods usually within the 24-72 hour time span, and all formulations are incubated for the same time. When the comparison is between free drug and carrier-formulated drug, especially for carriers that have specific positive interactions with the target cells, this same-incubation period skews the results in favor of the free drug. In vivo, the free drug will not remain for long in the target zone, whereas a targeted carrier may stay for prolonged periods. The short protocol is designed to modulate this free drug vs. carrier-drug imbalance towards the in vivo situation. Removal of the treatment media after 4 hours clears all extracellular free drug from the system, whereas the drug-loaded carriers can associated with the cells (bound to the membrane and/or endocytosed). If such associations take place, not all carrier-mediated drug is cleared upon removal of the treatment media at 4 hours and the remaining drug-carrier formulations can continue to supply the cells with drug throughout the remainder of the experiment.

For each cell line, it was verified that the gagomer concentrations used (there was no need to go above gagomer concentration range of 1.5 mg PE/ml) were not toxic to the cells. The data of cell viability as a function of paclitaxel concentrations were used to extract the IC$_{50}$ (drug concentration causing 50% inhibition of cell proliferation). This parameter is in wide use as the field-standard parameter potency—the lower the IC$_{50}$, the higher the potency of a given formulation.

Paclitaxel IC$_{50}$ values for free and for gagomer-loaded drug are listed in Table 5. In all cases, and for the three different paclitaxel-gagomer types of formulation, the data show quite clearly that the encapsulated paclitaxel remains active. For both the via-DMSO and the via-ethanol formulations there is no significant difference between the free and the carrier-formulated drug.

TABLE 5

Cytotoxicity of free and gagomer-encapsulated paclitaxel

| TX-GAG Formulation Method | Cell line | $IC_{50}$ short protocol[1] (µM paclitaxel) | | $IC_{50}$ long protocol (µM paclitaxel) | |
|---|---|---|---|---|---|
| | | Free Paclitaxel[2] | TX-GAG[3] | Free Paclitaxel | TX-GAG |
| Via-DMSO | B16F10.9[4] | 0.2 | 0.6 | 0.03 | 0.04 |
| | D122 | 0.9 | 3.0 | 0.25 | 0.25 |
| | C-26 | 3.0 | 4.0 | 3.5 | 5.0 |
| | PANC-1 | 0.3 | 0.3 | 0.02 | 0.04 |
| | COS-7 | 1 | 1 | 0.06 | 0.12 |
| Via-Ethanol | SNU-251 | 0.6 | 0.9 | 0.25 | 0.15 |
| Via-PE | B16F10.9 | 1.8 | 0.4 | 0.12 | 0.22 |
| | COS-7 | >40 | 20 | 5 | 5 |

[1]Short protocol: 4 hours of incubation with treatment media, then: aspiration, wash, incubation for additional 44 hours in drug-free serum-supplemented cell growth media. Long protocol: 48 hours of incubation with the treatment media.
[2]Free paclitaxel diluted directly into medium
[3]TX-GAG: Paclitaxel-encapsulating gagomers
[4]Cell origin and type:
B16F10.9: mouse melanoma, subline of B16F10, MDR, over-expressing hyaluronan receptors
D122: subline of mouse lung Lewis carcinoma, MDR, over-expressing hyaluronan receptors
C-26: mouse colon carcinoma, MDR, over-expressing hyaluronan receptors
PANC-1: human pancreatic adenocarcinoma, MDR, over-expressing hyaluronan receptors
COS-7: Green African monkey kidneys, subline of CV-1. Non-tumor cells and poor-expressers of hyaluronan receptors
SNU-251: Human ovarian cancer, no reports found in the literature with respect to hyaluronan receptors or MDR status.

The results with the via-PE formulation, are also listed in Table 5. These results are the most encouraging of the lot. They show quite clearly that in the short protocol (which is the more relevant one when comparing free vs. carrier-formulated drug) there is a drop-down in $IC_{50}$ values. Hence, the increase in potency from the free to the gagomer-formulated drug of more than 4 fold. Taking into account the above-discussed mechanisms of drug supply to the cells, the increase in potency when formulated in gagomers may be even higher. Moreover, the increase in the tumor cell line is significantly higher than in the control, non-tumor line.

Example 8

Preparation and Characterization of Paclitaxel-Loaded Gagomers

Initial Drug Dissolution in Ethanol, Followed by Addition to Ethanolic DPPE Solution (Referred to as the Via Ethanolic-DPPE Method)

This approach is similar to that of Example 3, with the following differences:
(1) The lipid, dipalmitoyl phosphatidylethanolamine (DPPE), was dissolved in ethanol at 55° C., to a concentration of 12 mg PE/ml.
(2) a stock concentration of paclitaxel was dissolved in ethanol and added to the ethanolic DPPE solution, and the combined DPPE/taxol ethanolic solution was kept at 55° C., for 15 additional minutes.
(3) The DPPE/taxol ethanolic solution was evaporated to dryness and dispersed in the basic borate buffer as described in steps 2 of Example 1, except that the incubation of this dispersion was at 65° C. From this point, the process continued as in Example 3. Efficiency of paclitaxel was complete (i.e., 100%). Cytotoxicity in B16D10.9 cells was determined as described in Example 7. The results, shown in the first row of Table 6, show that the gagomer-encapsulated paclitaxel retained activity and is more potent (i.e., lower $IC_{50}$) than free paclitaxel. Ethanolic solutions of paclitaxel were heated at several temperatures within the range of 40-70° C., under the same conditions used for making the paclitaxel-encapsulating gagomers in the method of this example, and using the same cytotoxicity assay, it was verified that, under the present conditions, the heating did not impair the drug's cytotoxic activity.

TABLE 6

Cytotoxicity of free and gagomer-encapsulated paclitaxel, ethanol as the lipid solvent, in B16F10.9 cells.

| TX-GAG Formulation Method | $IC_{50}$ short protocol[1] (µM paclitaxel) | |
|---|---|---|
| | Free Paclitaxel[2] | TX-GAG[3] |
| Via Ethanolic-DPPE | 1.8 | 1.1 |
| Via Ethanolic-DLPE | 1.8 | 0.15 |

[1]Short protocol: 4 hours of incubation with treatment media, then: aspiration, wash, incubation for additional 44 hours in drug-free serum-supplemented cell growth media. Long protocol: 48 hours of incubation with the treatment media.
[2]Free paclitaxel diluted directly into medium
[3]TX-GAG: Paclitaxel-encapsulating gagomers Example 9

Preparation and Characterization of Paclitaxel-Loaded Gagomers

Initial Drug Dissolution in Ethanol, Followed by Addition to Ethanolic DLPE Solution (Referred to as the Via Ethanolic-DLPE Method)

Gagomer preparation and paclitaxel encapsulation were all similar to that described Example 8, except for the following:
(1) DPPE, that has two palmitoyl chains (i.e., C16), was replaced by another PE—DLPE, in which the two chains are dilauryl (i.e., C12).
(2) The temperature for the lipid dissolution in ethanol, for the mixing of the ethanolic lipid solution with the ethanolic paclitaxel solution, and the temperature for the 2 hour incubation for the dispersion of the DLPE and the paclitaxel in the basic borate buffer were all lowered to 44° C. All other steps were similar to those of Example 8.
Efficiency of paclitaxel was complete (i.e., 100%). Cytotoxicity, in B16D10.9 cells was determined as described in Example 7. The results, shown in the second row of Table 6, show that the gagomer-encapsulated paclitaxel retained activity, and is more potent (i.e., lower $IC_{50}$) than the free paclitaxel. Among all paclitaxel-gagomer formulations made to date, this formulation (see Tables 5 and 6), was the best in terms of preparation, encapsulation efficiency and cytotoxicity.

Example 10

Drug Loading Capacity of TX-GAG Particles

TX-GAG particles were prepared, using DLPE as the lipid, according to the scheme outlined in FIG. 7. Initial drug/lipid mole ratios ranged from 1:10 (i.e., 0.1) to 1:2 (i.e., 0.5)

TX:lipid, and encapsulation efficiency was determined for each of these preparations, by centrifugations and washings, as described Example 1.

To evaluate whether the paclitaxel in the centrifuged pellets is completely within the gagomer particle, or some of it—especially as the drug loading is increased—remains as free insoluble drug outside the particle, the washing of the TX-GAG particles from excess reagents which is done by high speed centrifugation, (step 5 in FIG. 7) was done as follows: Each preparation was divided into two parts. One part was centrifuged and washed, as in the previous examples, with phosphate-buffered saline (PBS) alone. The other part was centrifuged and washed under similar conditions, but the wash media was PBS containing 0.2% Bovine-serum albumin (BSA). The rationale for using the latter stems not only from the traditional use of this protein as a generic "contaminant absorbing protein", but specifically because paclitaxel has high affinity to this protein and serum albumin acts as the endogenous carrier of the free paclitaxel given to patients in the commercial formulation currently in use. If the centrifuged pellets contained drug which did not enter into the gagomer particles and, due to its insolubility, precipitated in the pellet together with the TX-GAG particles, the BSA should have dissolved at least some of the precipitated free drug. This removal of precipitated free paclitaxel from pellet into the supernatant would reduce the drug in the centrifuged pellet, compared to the equivalent system washed with PBS alone.

Figure 8:
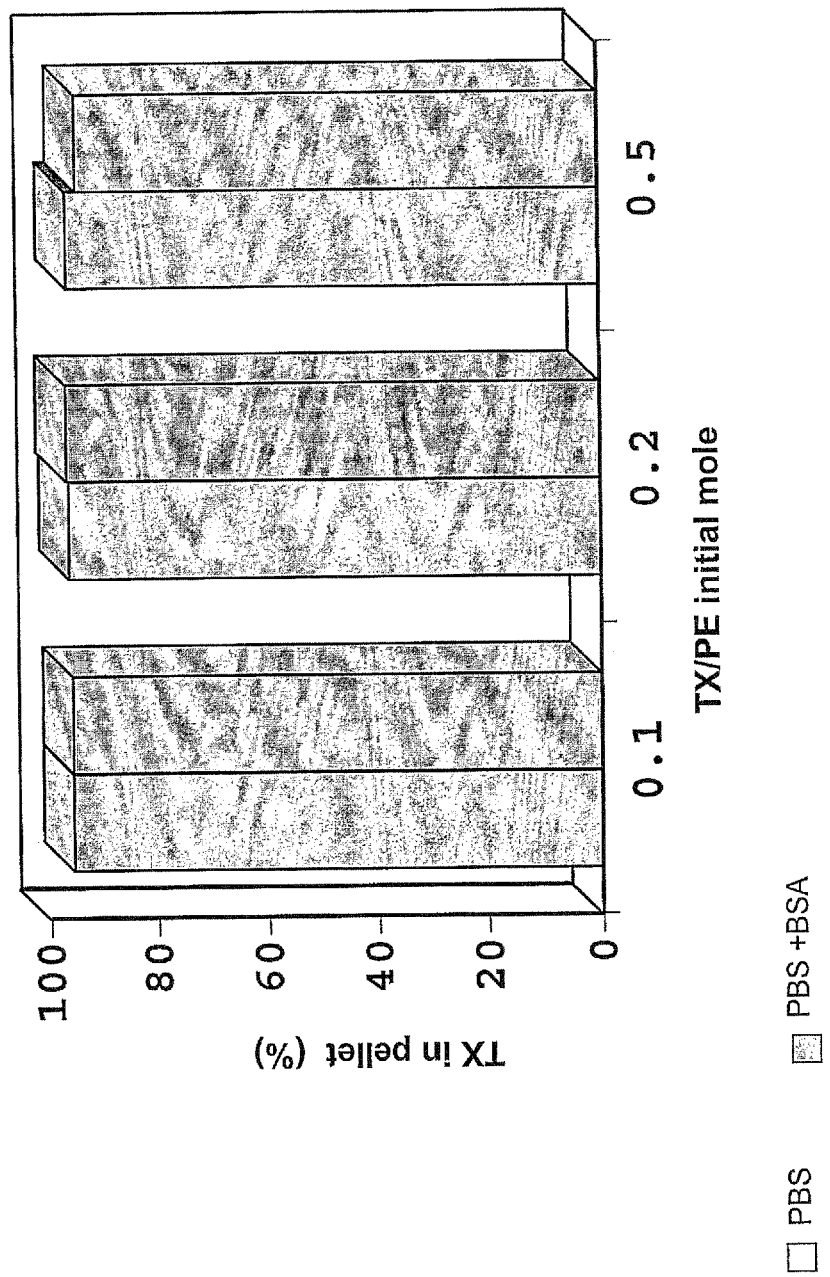
FIG. 8 is a graph showing retention of paclitaxel (TX) in centrifuged pellet washed with phosphate-buffered saline alone (light bars), or the same buffer but also containing 0.2% bovine serum albumin (dark bars).

The results, shown in FIG. 8, make it quite clear that the BSA wash did not diminish the drug in the pellet, thus indicating that for all loads—all the paclitaxel associated with the gagomers is indeed loaded inside gagomers. Higher BSA concentrations (3%) also did not "wash out" paclitaxel from the TX-GAG particles.

Example 11

Calorimetric Analysis of TX-GAG Particles

TX-GAG particles, with drug/lipid mole ratios ranging from 1:10 to 1:2 were prepared as described in Example 10. Drug-free gagomers were similarly prepared, omitting the drug. Both types of systems were lyophilized, as described in step 6 of FIG. 7.

Within the temperature range of 230-250° C., crystalline paclitaxel, as well as paclitaxel lyophilized from aqueous suspensions (denoted hydrated paclitaxel), are known to undergo first melting, then decomposition. It is further known that the melting is an endothermic process and the decomposition is an exothermic process. Both processes, and their successive pattern of first an endothermic peak, followed by an exothermic peak, can be determined and viewed by subjecting the matter to Differential Scanning Calorimetry (DCS). This is exemplified by the two scans, one for crystalline, and the other for hydrated, paclitaxel, in the upper part of FIG. 9.

Figure 9:
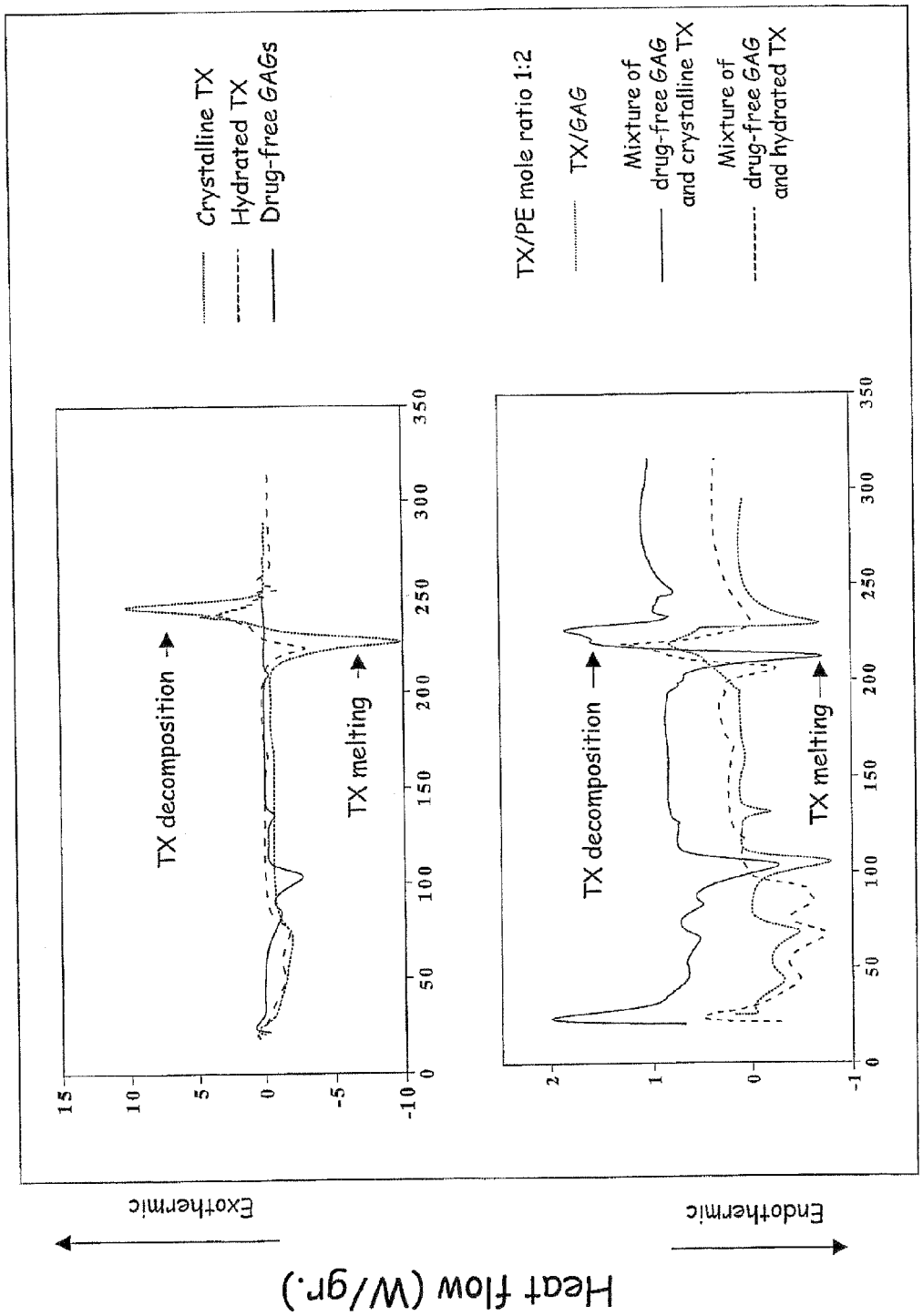
FIG. 9 shows differential scanning calorimetry of drug-loaded and drug-free gagomers, as well as free drug. Upper part: free paclitaxel—crystalline (dotted line) and hydrated (dashed line) and of drug-free gagomers (solid black line). Lower part: mixtures of free crystalline (solid black line) or hydrated (dashed line) paclitaxel with drug-free gagomers, at drug:lipid mole ratios of 1:2. Paclitaxel-loaded gagomers (dotted line) also at the drug:lipid mole ratio of 1:2.

As also shown in the upper part of FIG. 9, drug-free gagomers subjected to DSC were found to have a small endothermic peak in the region of 100° C., attributed to the lipid, but to undergo no thermal changes in the 230-270° C. range where free paclitaxel undergoes, as shown and discussed above, massive changes. Mixtures of drug-free gagomers and crystalline or hydrated paclitaxel, at drug:lipid mole ratio of 1:2, were also subjected to DSC. As exemplified in the lower part of FIG. 9, the independent components in the mixture retained their individual thermal behaviors, showing the lipid endothermic peak at the region of 100° C., and the two successive endothermic and exothermic peaks in the 230-250° C. range.

In contrast to all of the above, subjecting TX-GAG formulations to DCS, revealed a different thermal behavior for the encapsulated (compared to free) drug. As also shown in the lower part of FIG. 9, for a drug loading of 1:2 TX:PE, the melting peak of paclitaxel disappeared whereas the decomposition peak remained. Similar results were obtained with lower drug:lipid loadings.

For all samples, the identification of the decomposition peak was also done by Thermogravimetric Analysis (TGA).

All the above results together fit with the findings of Example 10, strongly indicating that a TX-GAG particle with exceptionally high drug loading is obtained.

Example 12

Paclitaxel Stability in Sterilized TX-GAG Particles

Figure 10:
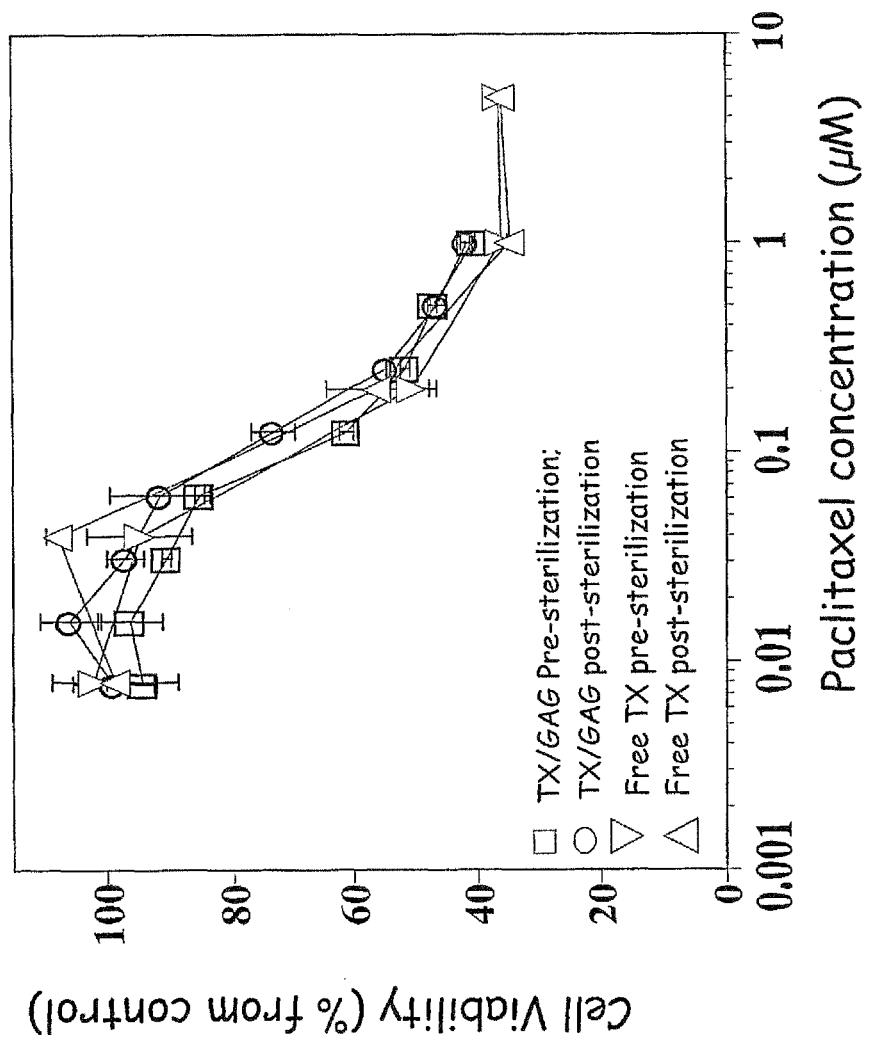
FIG. 10 is a graph showing cytotoxicity of free paclitaxel and of paclitaxel-loaded gagomers, before and after sterilization, in cultures of B16F10.9 cells.

Aqueous suspensions of TX-GAG particles were prepared according to the scheme of FIG. 7, up to and including step 5. Aqueous suspensions of paclitaxel alone (i.e., free paclitaxel) were also prepared. Samples were set aside, from both the TX-GAG and the free paclitaxel, and the remainder of each system was subjected to the following sterilization process: 12 minutes of autoclaving at 120° C. A critical question of whether this sterilization process is feasible for the TX-GAG formulations, is retention of drug activity. Therefore, the original samples set aside prior to the sterilization process, as well as the samples that underwent the process, were tested for their cytotoxicity, in B16F10.9 cultures, as described in Example 7. As shown by the results illustrated in FIG. 10, and as expected, the sterilization process did not generate any significant drop in the cytotoxicity of free paclitaxel. Moreover, this process also did not cause any significant drop in the cytotoxicity of the gagomer-loaded paclitaxel. In fact, all four systems were similar in cytotoxicity, the $IC_{50}$ value in the range of 0.30 µM paclitaxel.

These results indicate that the TX-GAG formulation had good stability under the sterilization conditions applied, and further indicate that this is a feasible approach to product sterilization.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

R. Margalit, R. Alon, M. Linenberg, I. Rubin, T. J. Roseman, R. W. Wood. Liposomal drug delivery: thermodynamic and chemical kinetic considerations. J. Controlled Release 17:285-296 (1991)

What is claimed is:

1. A method for treating a subject suffering from cancer, wherein the cancer cells have a glycosaminoglycan recognition site, comprising administering to said subject an effective amount of a water insoluble or poorly water soluble anticancer drug for treating said cancer, which is encapsulated in a water insoluble lipidated glycosaminoglycan particle, wherein:
    the lipidated glycosaminoglycan particle comprises the reaction product of at least one glycosaminoglycan with at least one lipid having a primary amino group to form a shell of glycosaminoglycan on the outside of the particle with the lipid portion of the particle forming the inside, without the presence of liposomes; and
    the ratio of lipid to glycosaminoglycan is in the range of 1:1 and 5:1 to 20:1.

2. The method of claim 1, wherein the cancer is selected from the group consisting of ovarian cancer, breast cancer, colon cancer, head cancer, non-small cell lung carcinoma, and AIDS-associated Kaposi sarcoma.

3. The method of claim 2, wherein the water insoluble or poorly water soluble active ingredient is paclitaxel.

4. The method of claim 3, wherein said at least one lipid is dilauryl phosphatidylethanolamine.

5. The method of claim 1, wherein said at least one glycosaminoglycan is selected from the group consisting of hyaluronic acid, keratan sulfate, chondroitin sulfate, heparin sulfate, heparan sulfate, dermatin sulfate, salts thereof, and mixtures thereof.

6. The method of claim 1, wherein said at least one glycosaminoglycan is hyaluronic acid.

7. The method of claim 1, wherein said at least one lipid is a phosphatidylethanolamine.

8. The method of claim 7, wherein said phosphatidylethanolamine is dipalmitoyl phosphatidylethanolamine.

9. The method of claim 7, wherein said phosphatidylethanolamine is dilauryl phosphatidylethanolamine.

10. The method of claim 1, wherein the size of the lipidated glycosaminoglycan particle is in a range of about 2-5 microns.

11. The method of claim 1, wherein the size of the lipidated glycosaminoglycan particle is in a range of about 50-200 nanometers.

12. The method of claim 1, wherein said at least one glycosaminoglycan has a molecular weight within a range of about $1 \times 10^5$ to about $1 \times 10^7$ daltons.

13. The method of claim 1, wherein the lipidated glycosaminoglycan particle is in the form of a sphere.

14. The method of claim 1, wherein the water insoluble or poorly water soluble active ingredient is selected from the group consisting of cisplatin, etoposide and fluorouracil.

15. A method for targeted delivery of a water insoluble or poorly water soluble bioactive agent to a cell having a glycosaminoglycan recognition site, comprising administering the water insoluble or poorly water soluble bioactive agent encapsulated in a water insoluble lipidated glycosaminoglycan particle in the form of a sphere with the glycosaminoglycan portion of the particle forming a shell on the outside and the lipid portion of the particle forming the inside, without the presence of liposome, said particle comprising the reaction product of at least one glycosaminoglycan with at least one lipid having a primary amino group,
    wherein:
    the glycosaminoglycan in the glycosaminoglycan particle corresponds to the glycosaminoglycan recognition site on the cell to which the bioactive agent is to be delivered; and
    the ratio of said at least one lipid having a primary amino group to said at least one glycosaminoglycan is in the range of 1:1 and 5:1 to 20:1.

16. The method of claim 15, wherein said at least one lipid is dilauryl phosphatidylethanolamine.

17. The method of claim 15, wherein said at least one glycosaminoglycan is selected from the group consisting of hyaluronic acid, keratan sulfate, chondroitin sulfate, heparin sulfate, heparan sulfate, dermatin sulfate, salts thereof, and mixtures thereof.

18. The method of claim 15, wherein said at least one glycosaminoglycan is hyaluronic acid.

19. The method of claim 15, wherein said at least one lipid is a phosphatidylethanolamine.

20. The method of claim 19, wherein said phosphatidylethanolamine is dipalmitoyl phosphatidylethanolamine.

21. The method of claim 19, wherein said phosphatidylethanolamine is dilauryl phosphatidylethanolamine.

22. The method of claim 15, wherein the size of the lipidated glycosaminoglycan particle is in a range of about 2-5 microns.

23. The method of claim 15, wherein the size of the lipidated glycosaminoglycan particle is in a range of about 50-200 nanometers.

24. The method of claim 15, wherein said at least one glycosaminoglycan has a molecular weight within a range of about $1 \times 10^5$ to about $1 \times 10^7$ daltons.

* * * * *